United States Patent
Ergun et al.

(10) Patent No.: US 6,298,109 B1
(45) Date of Patent: Oct. 2, 2001

(54) X-RAY IMAGING SYSTEM

(75) Inventors: David L. Ergun, Verona; David R. Strait, Madison, both of WI (US); Cornelis H. Slump, Oldenzaal (NL); Geert Jan Laanstra, Almelo (NL); Hendrik Kuipers, Hengelo (NL); Marcel J. Dijkstra, Nijverdal (NL); Hans Sjoerd Peter van der Schaar, Madison, WI (US)

(73) Assignee: Lunar Corporation, Madison, WI (US)

(*) Notice: Subject to any disclaimer, the term of this patent is extended or adjusted under 35 U.S.C. 154(b) by 0 days.

(21) Appl. No.: 09/416,351

(22) Filed: Oct. 12, 1999

Related U.S. Application Data

(63) Continuation-in-part of application No. 09/003,013, filed as application No. PCT/US97/02770 on Feb. 21, 1997, now Pat. No. 6,018,565.
(60) Provisional application No. 60/011,993, filed on Feb. 21, 1996.

(51) Int. Cl.[7] .................................................. A61B 6/03
(52) U.S. Cl. .................................................. 378/4; 378/901
(58) Field of Search .................................. 378/4, 62, 901

(56) References Cited

U.S. PATENT DOCUMENTS

| | | | |
|---|---|---|---|
| 4,367,490 | 1/1983 | Riederer | 348/620 |
| 4,802,197 | 1/1989 | Juergens | 378/197 |
| 4,952,805 | 8/1990 | Tanaka | 250/327.2 |
| 5,012,504 | 4/1991 | McFaul et al. | 378/108 |
| 5,150,421 | 9/1992 | Morishita et al. | 382/6 |
| 5,164,993 | 11/1992 | Capozzi et al. | 382/6 |
| 5,263,074 | 11/1993 | Sakamoto | 378/98.2 |
| 5,336,880 | 8/1994 | Laclerc et al. | 250/214 |
| 5,388,138 | 2/1995 | Fujiwara | 378/108 |
| 5,416,818 | 5/1995 | Takahashi et al. | 378/98.7 |
| 5,467,380 | 11/1995 | De Jonge et al. | 378/98.2 |
| 5,574,764 | 11/1996 | Granfors et al. | 378/98.7 |
| 5,696,807 | 12/1997 | Hsieh | 378/109 |
| 5,771,269 | 6/1998 | Chao | 378/5 |
| 5,852,646 | * 12/1998 | Klotz et al. | 378/8 |
| 5,923,727 | * 7/1999 | Navab | 378/207 |
| 6,007,243 | * 12/1999 | Ergun et al. | 378/197 |
| 6,018,565 | * 1/2000 | Ergun et al. | 378/95 |

FOREIGN PATENT DOCUMENTS

| | | |
|---|---|---|
| 0 218 923 A2 | 9/1986 | (EP). |
| 0 283 255 A2 | 3/1988 | (EP). |

OTHER PUBLICATIONS

K. Machin and S. Webb, "Cone–beam x–ray microtomography of small specimens," *Phys. Med. Bio.* 39(10):1639–1657, 1994.

* cited by examiner

Primary Examiner—David V. Bruce
(74) Attorney, Agent, or Firm—Quarles & Brady LLP

(57) ABSTRACT

An x-ray imaging system provides automatic adjustment of x-ray tube voltage and current as deduced from two exposures at different voltages. Real-time image distortion removal and image rotation are accomplished by computer processing using a generalized image transformation polynomial. Scatter in the image is reduced by calculating a scatter map based on a blurring of the received image and normalizing the scatter map to point scatter measurements made with an x-ray occluder eliminating direct exposure of certain areas of the image. Improved signal to noise ratio in a moving x-ray image is provided by averaging stationary portions of the image over a longer time than the moving portions of the image. A non-linear white compression function further reduced image noise by transforming the raw image to a gray scale having equal noise intervals.

7 Claims, 9 Drawing Sheets

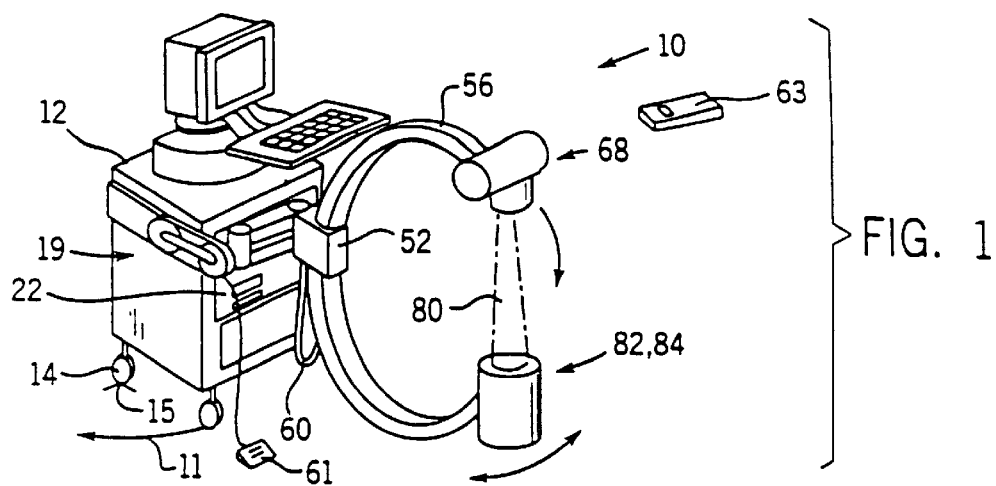
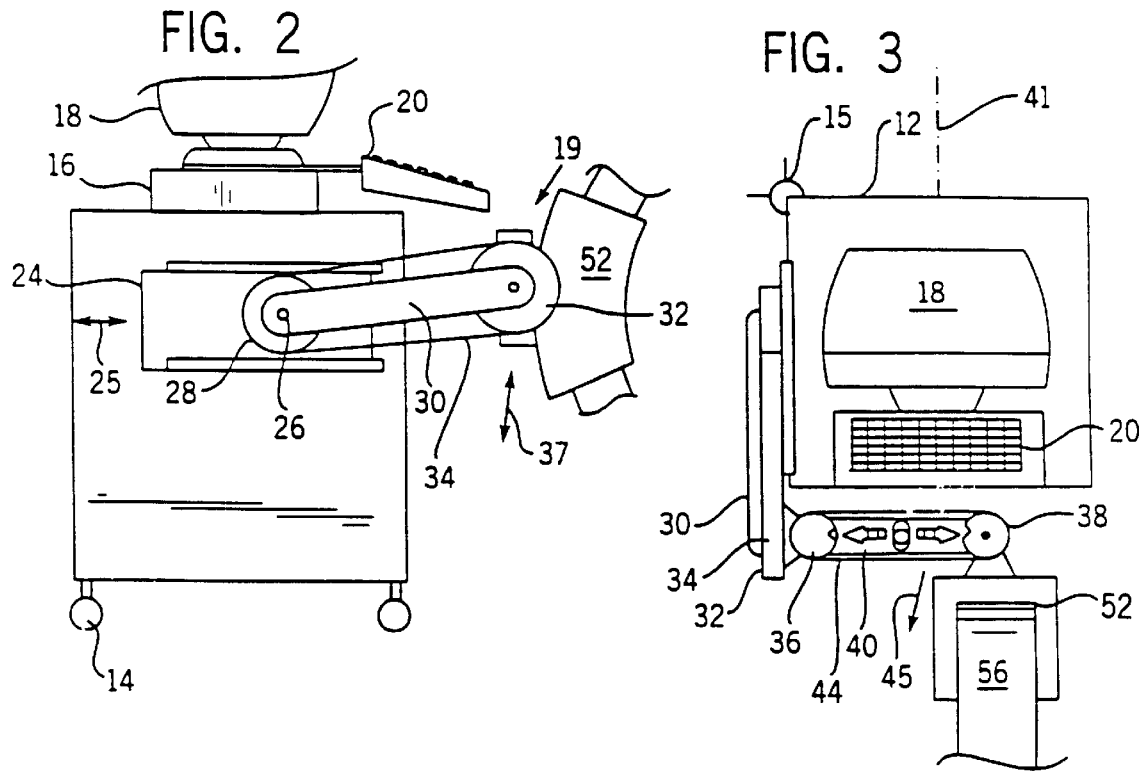
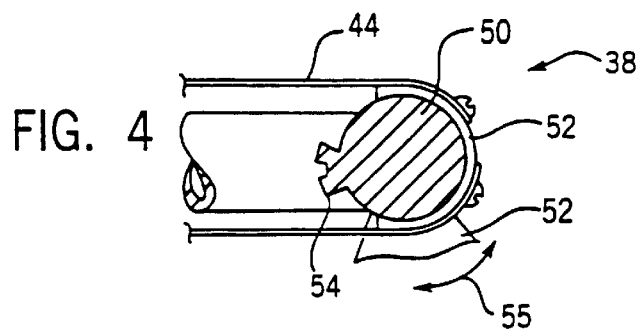

X-RAY IMAGING SYSTEM

CROSS-REFERENCE TO RELATED CASES

This application is a continuation-in-part of application Ser. No. 09/003,013 filed Jan. 5, 1998 now U.S. Pat. No. 6,018,565, issued Jan. 25, 2000 which claims the benefit of the provisional application Ser. No. 60/011,993 filed Feb. 21, 1996 and is a continuation of PCT application PCT/US97/02770 filed on Feb. 21, 1997. These applications are incorporated by reference herein.

FIELD OF THE INVENTION

The invention relates generally to x-ray equipment and in particular to x-ray equipment providing real-time imaging with rapid, automatic adjustment of x-ray voltage and current, and with image correction and image rotation.

BACKGROUND OF THE INVENTION

Current x-ray imaging systems may employ an x-ray tube providing a beam of x-rays emanating from a focal spot of the x-ray tube. The x-rays may be received by an image intensifier producing a visible image recorded by a video camera or the like. An object to be imaged is placed within the cone beam of x-rays and the video camera records an image indicating the attenuation of the x-ray beam by the imaged object.

An x-ray tube provides an electrical cathode within an evacuated envelope. Electrons generated at the cathode are accelerated against a target anode to produce x-rays. Controlling the electrical current generally affects the number of x-ray photons per unit time or fluence of the x-ray beam. Controlling the voltage between the cathode and anode affects the energy of each photon or the "hardness" of the x-rays.

In producing an x-ray image, it is often desirable to limit the dose to the extent possible. At the same time, it is desired that the imaging technique, i.e. the voltage across the tube and the current provided to the x-ray tube, be properly adjusted to provide an image with adequate detail. Generally, this adjustment considers the contrast in the image and its signal-to-noise ratio.

The correct technique varies considerably depending on the object being imaged. For medical imaging, it is known to provide certain preset techniques for different body parts. However, use of these presets requires the operator to identify the body part being imaged and will typically be less than optimum as a result of variations in particular patients and even the particular portion of the body part being imaged.

For many imaging situations where real-time imaging is required, it would be desirable to be able to turn the x-ray tube on and off on demand to obtain an instantaneous image and then to stop additional doses. The time required to adjust the proper technique for the particular imaged object is a significant obstacle to this goal.

Automatic exposure control (AEC) of an x-ray tube by varying the current to the x-ray tube based on the flux received by the image intensifier is known. Such AEC systems often work poorly when the imaged object is smaller than the field of view (FOV) of the system and therefore where some unattenuated x-rays are received by the image intensifier. In such cases, the AEC tends to overly decrease the x-ray fluence producing an image of the object that is too dark.

It is known to lower the total dose needed to produce a fluoroscopic image through the use of an image intensifier which uses electrical fields to accelerate photon produced electrons against a phosphorescent target. Such image intensifiers tend to distort the image. Such distortion detracts from the usefulness of the image when instruments are manipulated by an operator viewing the image, especially near the edges of the field of view. Distortion also adversely affects quantitative uses of the image such as morphometric or densiometric analysis.

X-ray imaging systems having movable x-ray tubes and image intensifiers may produce an image on a stationary monitor that appears to rotate depending on the orientation of the machine. Often the operator will desire that the rotational orientation of the image be corrected to provide more intuitive view of the object. This is particularly the case in medical systems where the x-ray image is used to guide medical instruments. Prior art has addressed this problem through the use of a motorized rotating camera or movable deflection yokes on the display screen itself. Both of these approaches provide real-time rotated images.

BRIEF SUMMARY OF THE INVENTION

The present invention provides a robust, automatic, technique-control for an x-ray tube that permits short exposures of an x-ray machine to be made without time consuming technique correction. Computerized analysis of the received image is used to identify the effect of changes in the technique on the image so that the correct technique may be rapidly selected.

Specifically, the present invention provides an x-ray imaging system having an x-ray source positioned on one side of an object to be imaged. The x-ray source is attached to an x-ray source power supply providing electrical energy to the x-ray source. An imaging x-ray detector is positioned on an opposite side of the object from the x-ray source and produces first x-ray reception signals each related to received x-rays passing along a path through the object; and second-x-ray reception signals each related to received x-rays passing along paths outside of the object. An electronic computer receiving the x-ray reception signals operates according to a stored program to identify the first x-ray reception signals and to control the x-ray tube power supply to adjust the exposure of the object based on the identified first x-ray reception signals.

Thus, it is one object of the invention to provide control of the exposure of the imaged object based only on the portion of the image attenuated by the object. By eliminating consideration of background portions of the image, exposure errors resulting from the imaging of small objects that only partially fill the field of view of the imaging system are eliminated.

The electronic computer may identify the first x-ray reception signals by constructing a histogram of signal values versus frequency of occurrence of particular signal values and identifying a peak within the histogram as second x-ray reception signals to be ignored.

Thus, it is another object of the invention to provide an easily automated method determining which portions of the image represent the imaged object when the imaged object may be in arbitrary size and dimension.

The electronic computer may control the x-ray tube power source to take at least two separate exposures of the object with different voltages applied to the x-ray tube to deduce a relationship between voltage and dose that may be used to determine an amperage and voltage to be applied to the X-ray tube.

Thus it is another object of the invention to provide an automatic technique adjustment system that may model the effect of changes in technique on changes in dose and thus more rapidly achieve the correct technique and dose.

The electronic computer may control the electrical power to the x-ray tube to decrease x-ray tube voltage for a given dose.

Thus, it is another object of the invention to identify a unique and consistent value of voltage and amperage among a variety of amperages and voltages that may produce the desired dose. It is further an object of the invention to select one voltage value that may be expected to generally improve tissue contrast.

The present invention employs an electronic computer to process the image data to remove distortion by mapping each point in the received image as stored in memory to a different point in the display according to a transform equation calculated in real-time by the electronic computer. Rotation of the image may be performed by treating the rotation as a form of distortion and adjusting the equation parameters to rotate the image appropriately.

Specifically, the invention provides a fluoroscopic x-ray imaging system having an x-ray tube positioned on one side of an object. Positioned on the opposite side of the object from the x-ray source is an imagining x-ray detector having an imaging surface and producing a plurality of x-ray reception signals, each related to x-rays received at the imaging surface at different spatial locations. An electronic display displays pixels at image locations and communicates with an electronic computer receiving the x-ray reception signals. The electronic computer operates according to a stored program to illuminate a pixel at a particular image location based on the value of a signal received at a particular spatial location. The particular image location and the particular spatial location are linked by a predetermined mathematical transformation correcting for at least one of the group consisting of rotation, isotropic distortion, and anisotropic distortion.

Thus it is one object of the invention to provide flexible image correction and rotation in an x-ray fluoroscopy machine. It is another object of the invention to use an electronic computer both to correct image distortion and to provide for image rotation in an x-ray fluoroscopy machine.

The transform pixels are always obtained from a stored copy of the received signals and their spatial locations.

Thus it is another object of the invention to permit repeated transformation and rotation of an x-ray fluoroscopy machine using mathematical techniques without degradation of the image resulting from truncation effects implicit in discrete mathematical techniques. Because the transformation always works off of a copy of the original image data, degradation of the image is avoided, for example, when repeated image rotations are made.

Other objects, advantages, and features of the present invention will become apparent from the following specification when taken in conjunction with the accompanying drawings.

BRIEF DESCRIPTION OF THE SEVERAL VIEWS OF THE DRAWINGS

FIG. 1 is a perspective view of the fluoroscopy machine of the present invention showing a C-arm supporting an image intensifier/video camera and x-ray tube in opposition for rotation in a vertical plane, the C-arm held along a mid-line of a cart by an articulated arm attached to the side of the cart;

FIG. 2 is a side view in elevation of the cart of FIG. 1 showing a slide attaching the articulated arm to the side of the cart and showing a four-bar linkage motion of the arm for elevation of the C-arm;

FIG. 3 is a top view of the C-arm system of FIG. 1 with the articulated arm in partial phantom showing the four-bar linkage of the arm for extending the C-arm toward and away from the cart;

FIG. 4 is a detail fragmentary view of an outer pivot of the articulated arm attached to the C-arm such as allows limited pivoting of a plane of rotation of the C-arm about a vertical axis;

DETAILED DESCRIPTION OF THE INVENTION

C-Arm Support Mechanism

Figure 5:
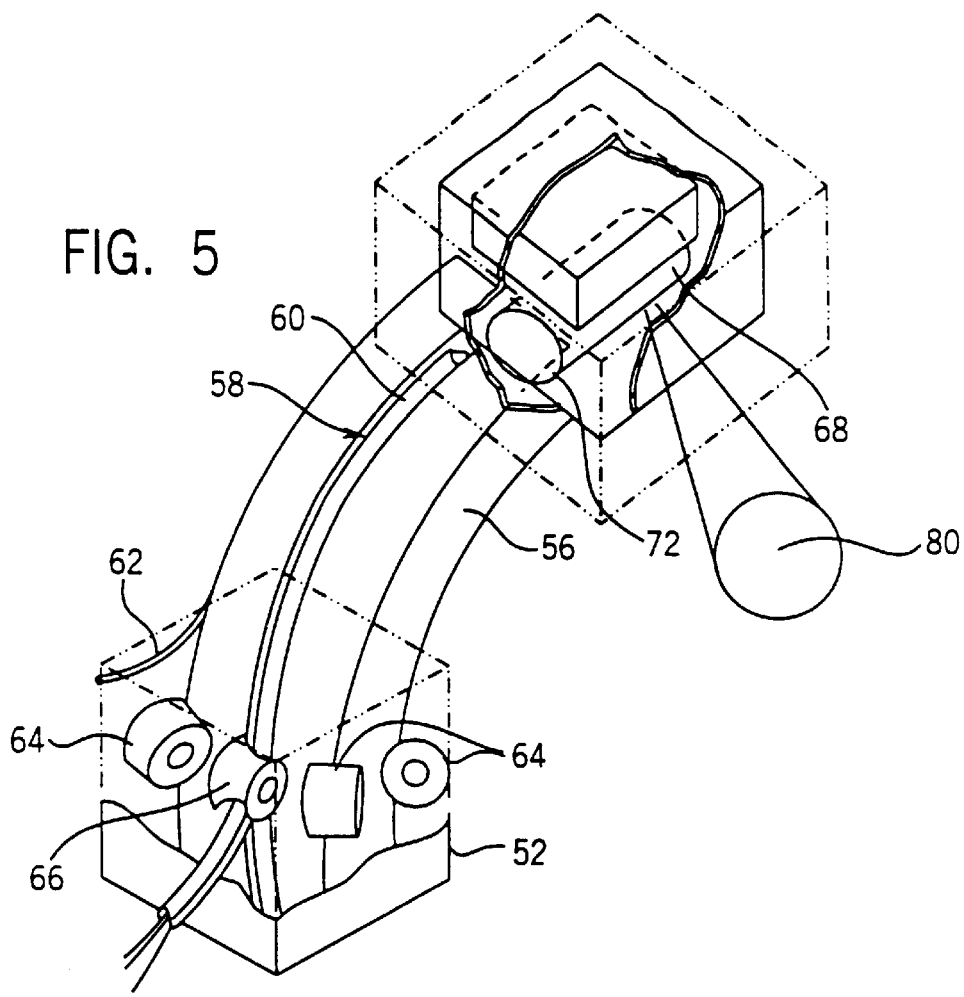
FIG. 5 is a detail view of the C-arm of FIG. 1 and the attached x-ray tube assembly showing the electrical cabling providing power to an x-ray tube power supply fitting into a groove in the C-arm and showing an abutment of the anode of the x-ray tube against the metal casting of the C-arm for heat sinking purposes.

Referring now to FIG. 1, an x-ray machine 10 per the present invention includes a generally box-shaped cart 12 having castors 14 extending downward from its four lower corners. The castors 14 have wheels rotating about a generally horizontal axis, and swiveling about a generally vertical axis passing along the edges of the cart 12. Castors 14, as are understood in the art, may be locked against swiveling and/or against rotation.

With one castor 14 locked and the others free to rotate and swivel, a pivot point 15 for the cart 12 is established with respect to the floor such as may be used as a first positioning axis 11 for the x-ray machine 10.

Positioned on the top of the cart 12 is a turntable 16 holding a computer monitor 18 and attached keyboard 20 for swiveling about a vertical axis for convenience of the user. The computer monitor 18 and the keyboard 20 may swivel separately so that one operator may view the computer monitor 18 while a second operates the keyboard 20.

The computer monitor 18 and the keyboard 20 allow for control of a computer 22 contained in a shelf on the cart 12 open from the front of the cart 12. The computer 22, the computer monitor 18, and the keyboard 20 are conventional "PC" type components well understood to those of ordinary skill in the art. The computer 22 further includes a number of interface boards allowing it to provide control signals to various components of the x-ray machine 10 as will be described and to receive x-ray image data. In addition, the computer 22 receives signals from a foot switch 61 that is used to activate the x-ray system for a brief exposure. Control of the computer 22 may also be accomplished through a remote control wand 63 of a type known in the art.

Referring now also to FIG. 2, attached to the right side of the cart 12 is a horizontal slide 24 positioned to provide an attachment point 26 for an articulated arm 19 supporting a C-arm 56, which in turn holds an x-ray tube 68 and an image intensifier 82 and camera 84, in opposition, as will be described below.

The articulated arm 19 may be slid horizontally toward the front of the cart 12 to provide a second positioning axis 25 of the x-ray machine 10. A first pulley 28 is rotatively fixed in a vertical plane, attached to the portion of the slide 24 that may move with respect to the cart 12, and is pivotally attached to a rigid arm 30 extending toward the front of the cart 12. The other end of the rigid arm 30 supporting a second pulley 32 is also mounted to swivel with respect to arm 30. A belt 34 wraps around a portion of the circumference of each of pulleys 28 and 32 and is affixed at one point along that circumference to each of the pulleys 28 and 32 so that pivoting motion of the arm 30 about the center point 26 of pulley 28 causes rotation of pulley 32 so that it maintains a fixed rotational orientation with respect to the cart 12 as pulley 32 and hence C-arm 56 is moved up and down along a third positional axis 37. The linkage, so created, is a variation of the "four bar linkage" well known in the art.

Helical tension springs (not shown for clarity) balance the pulley 32 in rotative equilibrium about point 26 against the weight of the articulated arm 19, C-arm 56, and other devices attached to the arm 19.

Attached to pulley 32 is a third pulley 36 extending in a generally horizontal plane perpendicular to the plane of pulley 32. The third pulley 32 is attached pivotally to a second rigid arm 40 which at its other end holds another pulley 38 positioned approximately at the midline 41 of the cart 12. The midline 41 symmetrically divides the left and right sides of the cart 12.

Portions of the circumference of pulleys 36 and 38 are also connected together by a belt 44 so as to form a second four bar linkage allowing pulley 38 to move toward and away from the cart 12, along a fourth positioning axis 45, with pulley 38 and C-arm 56 maintaining their rotational orientation with respect to cart 12.

Referring now to FIG. 4, pulley 38 includes a center shaft member 50 having a coaxial outer collar 52 to which belt 44 is attached. A stop 54 attached to the shaft 50 limits the motion of the collar 52 in rotation with respect to the shaft 50 to approximately 26 degrees. Frictional forces between shaft 50 and collar 52 cause shaft 50 to maintain its rotational orientation with respect to collar 52 and hence with respect to pulley 36 until sufficient force is exerted on shaft 50 to displace it with respect to collar 52. Thus pressure on the C-arm 56 can provide some pivoting motion of the C-arm about the axis of the pulley along the fifth positional axis 55.

Referring now to FIGS. 1, 3 and 4, attached to the shaft 50 is a C-arm collar 52 supporting the arcuate C-arm 56 curving through an approximately 180 degree arc in a vertical plane substantially aligned with the midline 41 of the cart 12.

As described above, motion of the collar 52 may be had in a vertical manner by means of the parallelogram linkage formed by pulleys 28 and 32 of the articulated arm 19 as shown in FIG. 2. Forward and backward motion away from and toward the cart 12 may be had by the second four bar linkage formed from pulleys 36 and 38. A slight pivoting of the C-arm 56 about a vertical axis slightly to the rear of the collar 52 and concentric with the axis of pulley 38 may be had by means of the rotation between collar 52 and 50 of FIG. 4. Greater rotation of the C-arm about the vertical axis passing through pivot point 15 may be had by rotation of the cart about one of its stationary castors 14. Thus, considerable flexibility in positioning the C-arm may be had.

Referring now to FIG. 5, the C-arm 56 is an aluminum casting having formed along its outer circumference a channel 58 into which a cable 60 may be run as will be described. C-arm 56 has a generally rectangular cross-section taken along a line of radius of the C-arm arc. Each corner of that rectangular cross-section holds a hardened steel wire 62 to provide a contact point for corner bearings 64 within the collar 52. The corner bearings 64 support the C-arm 56 but allow movement of the C-arm 56 along its arc through the collar 52.

A cable guide pulley 66 positioned over the channel 58 and having a concave circumference feeds the cable 60 into the channel 58 as the C-arm moves preventing tangling of the cable 60 or its exposure at the upper edge of the C-arm 56 when the C-arm 56 is rotated. The excess length of cable 60 loops out beneath the collar 52.

X-Ray Tube Cooling

Referring now to FIGS. 5 and G, the C-arm supports at one end a generally cylindrical x-ray tube 68 having a cathode 70 emitting a stream of electrons against a fixed anode 72. The conversion efficiencies of x-ray tubes are such that the anode 72 can become quite hot and typically requires cooling. In the present invention, the anode 72 is positioned to be bolted against the aluminum casting of the C-arm 56 thereby dissipating its heat into a large conductive metal structure of the C-arm 56.

The x-ray tube 68 is connected to a x-ray tube power supply 74 which separately controls the current and voltage to the x-ray tube 68 based on signals received from the computer 22 as will be described. The control signals to the x-ray tube power supply 74 are encoded on a fiber optic within the cable 60 to be noise immune. Low voltage conductors are also contained within cable 60 to provide power to the x-ray tube power supply 74 from a low voltage power supply 76 positioned on the cart 12.

During operation, an x-ray beam 80 emitted from the x-ray tube 68 passes through a patient (not shown) and is received by an image intensifier 82 and recorded by a charge couple device ("CCD") camera 84 such as is well known in the art. The camera provides digital radiation values to the computer 22 for processing as will be described below. Each radiation value describes the intensity of x-ray radiation received at a specific point on the imaging surface of the image intensifier 82.

Image Noise Reduction

Figure 6:
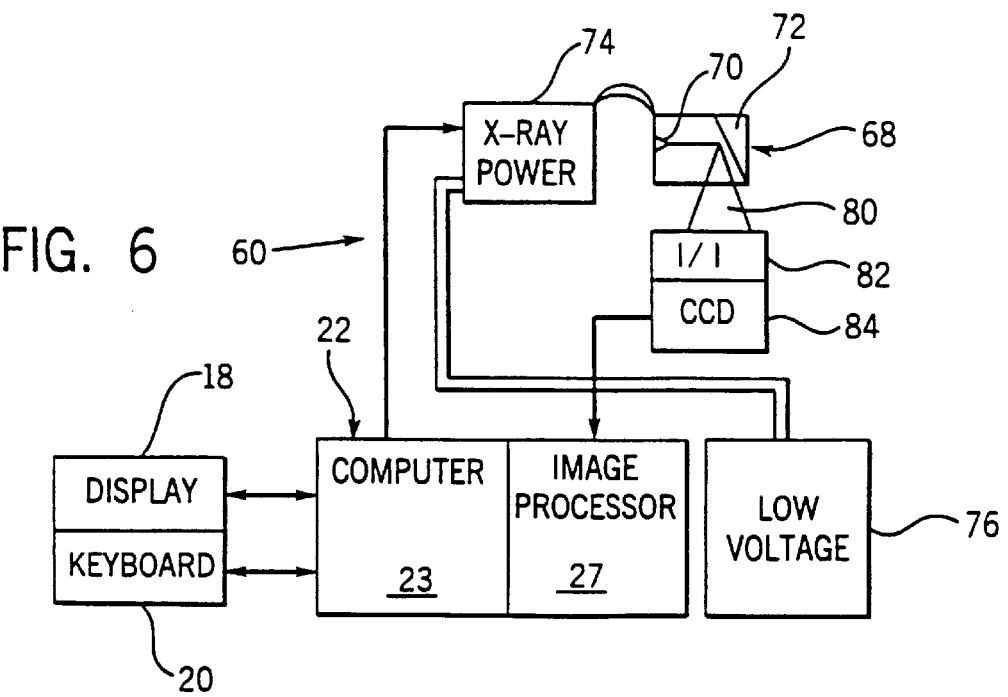
FIG. 6 is a schematic block diagram of the fluoroscopy machine of FIG. 1 showing the path of control of a remote x-ray tube power supply by a microprocessor and the receipt of data from the image intensifier/video camera by the microprocessor for image processing.
Figures 7, 8:
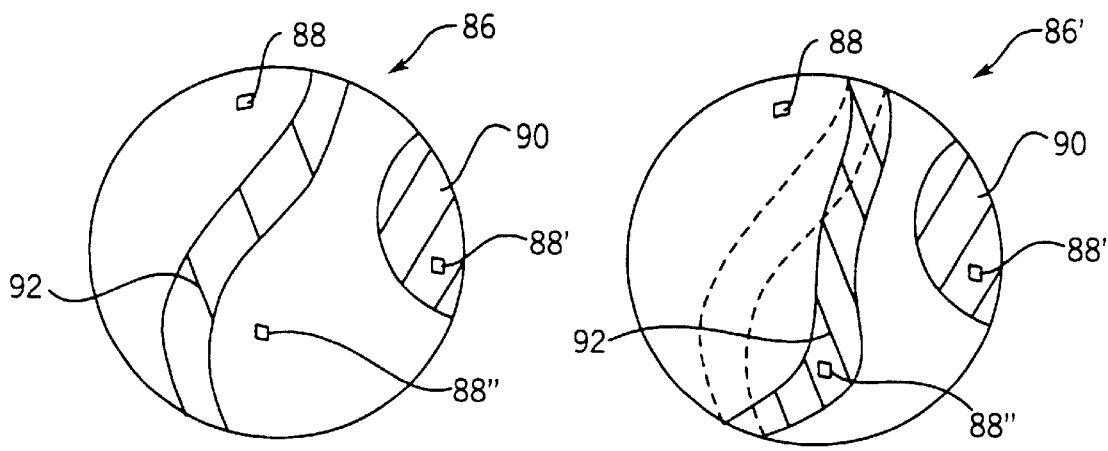
FIGS. 7 and 8 are simplified images such as may be obtained by the system of FIG. 1 showing portions of the image having moving elements and portions having stationary elements.

Referring now to FIGS. 6 and 7, the data collected by the CCD camera 84 may be used to provide an image 86 displayed on computer monitor 18. As will be described in more detail below, the CCD camera receiving a light image from the image intensifier 82 at a variety of points, provides data to the computer which maps the data from the CCD camera 84 to a pixel 88 in the image 86. For convenience, the data from the CCD camera 84 will also be termed radiation data reflecting the fact that there is not necessarily a one-to-one correspondence between data detected by the CCD camera 84 and pixels 88 displayed on the computer monitor 18.

The CCD camera 84 provides a complete set of radiation data for an entire image 86 (a frame) periodically once every "frame interval" so that real-time image of a patient placed within the x-ray beam 80 may be obtained. Typical frame rates are in the order of thirty frames per second or thirty complete readouts of the CCD detector area to the computer 22 each second.

Each frame of data is stored in the memory of the computer 22 and held until after complete storage of the next frame of data. The memory of the computer 22 also holds an average frame of data which represents a historical averaging of frames of data as will now be described and which is normally used to generate the image on the computer monitor 18.

In a typical image 86, there will be some stationary object 90 such as bone and some moving object 92 such as a blood vessel. In a second image 86' taken one frame after the image 86, the bone 90 remains in the same place relative to the edge of the image 86 and 86', however the blood vessel 92 has moved. Accordingly, some pixels 88' show no appreciable change between images 86 and 86', whereas some other pixels 88" show a significant change between images 86 and images 86'.

Figure 9:
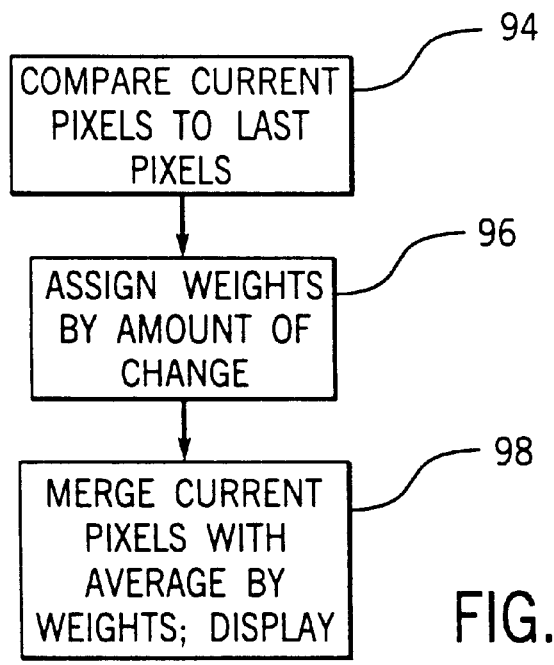
FIG. 9 is a flow chart of a method of the present invention providing differently weighted noise reduction to different areas of the image based on motion in the areas of the image.

Referring now to FIG. 9, as data arrives at the computer 22, the computer 22 executes a stored program to compare current pixels of the image 86' to the last pixels obtained from image 86 as indicated by process block 94. This comparison is on a pixel by pixel basis with only corresponding pixels in the images 86 and 86' compared. The difference between the values of the pixels 88, reflecting a difference in the amount of x-ray flux received at the CCD camera 84, is mapped to a weight between zero and one, with greater difference between pixels 88 in these two images corresponding to larger values of this weight w. This mapping to the weighting is shown at process block 96.

Thus pixels 88", whose value changes almost by the entire range of pixel values between images 86 and 86', receive a weighting of "one" whereas pixels 88' which have no change between images 86 and 86' receive a value of zero. The majority of pixels 88 being neither unchanged nor radically changed will receive a value somewhere between zero and one.

Generally, because the amount of x-ray fluence in the beam 80 is maintained at a low level to reduce the dose to the patient, the images 86 and 86 will have appreciable noise represented as a speckling in the images 86 and 86'. This noise, being of random character, may be reduced by averaging data for each pixel 88 over a number of frames of acquisition effectively increasing the amount of x-ray contributing to the image of that pixel.

Nevertheless, this averaging process tends to obscure motion such as exhibited by blood vessel 92. Accordingly, the present invention develops an average image combining the values of the pixels acquired in each frame 86, 86' in which those pixels in the current image 86' which exhibit very little change between images 86 and 86' contribute equally to the average image, but those pixels in the current image 86' that exhibit a great degree of change between images 86 and 86' are given a substantially greater weight in the average image. In this process, a compromise is reached between using historical data to reduce noise and using current data so that the image accurately reflects changes. Specifically, the value of each pixel displayed in the image is computed as follows.

$$P_i=(1-w)P_i+wP_{i,t} \tag{1}$$

where $P_i$ is a pixel in the average image, w is the weighting factor described above and $P_{i,t}$ is the current data obtained from the CCD camera 84. This effective merger of the new data and the old data keyed to the change in the data is shown at process block 98.

Image Intensifier Distortion

Figure 10:
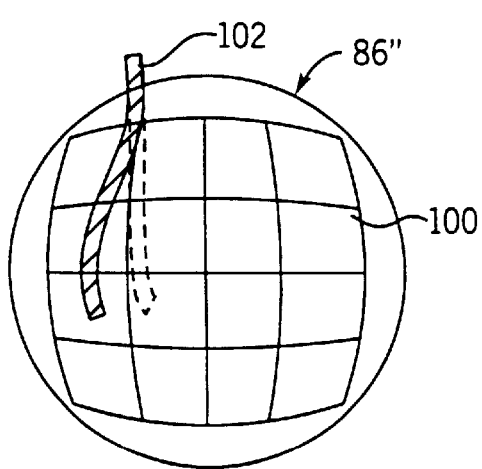
FIG. 10 is a FIG. similar to that of FIG. 7 showing an image of a rectilinear grid as affected by pincushion distortion in the image intensifier and video camera optics such as may provide a confusing image of a surgical tool being manipulated in real-time.

Referring now to FIG. 10, an image 86" of a rectilinear grid 100 positioned in the x-ray beam 80 will appear to have a barrel or pincushion shape caused by distortion of the image intensifier 82 and the optics of the CCD camera 84. During a real-time use of the image 86" by a physician, this distortion may cause confusion by the physician controlling a tool 102. For example, tool 102 may be a straight wire shown by the dotted line, but may display an image 86' as a curved wire whose curvature changes depending on the position of the tool 102 within the image 86. This distortion thus may provide an obstacle to a physician attempting to accurately place the tool 102 with respect to an object within the image 86'.

Figure 11:
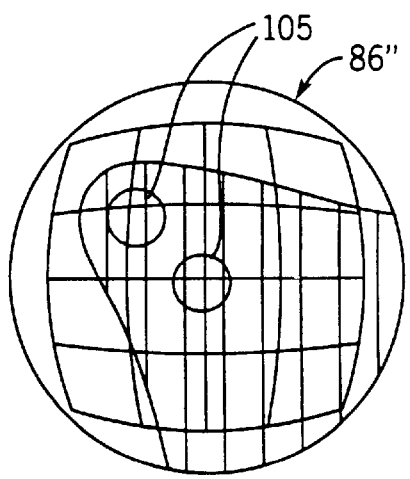
FIG. 11 is a FIG. similar to FIG. 10 showing equal areas of the image that encompass different areas of the imaged object, such variation as may affect quantitative bone density readings.

Referring now to FIG. 11, the distortion of image 86" also means that two equal area regions of interest 105 (equal in area with respect to the image) do not encompass equal areas of the x-ray beam 80 received by the image intensifier 82. Accordingly, if the data from the CCD camera 84 is used for quantitative purposes, for example to deduce bone density, this distortion will cause an erroneous variation in bone density unrelated to the object being measured.

Accordingly, the present inventors have adopted a real-time digital re-mapping of radiation data from the CCD camera 84 to the image 86 to correct for any pincushion-type distortion. This remapping requires the imaging of the rectilinear grid 100 and an interpolation of the position of the radiation data received from the CCD camera 84 to new locations on the image 86" according to that test image. By using digital processing techniques in a dedicated image processor, this remapping may be done on a real-time basis with previously unobtained accuracy.

Figure 19:
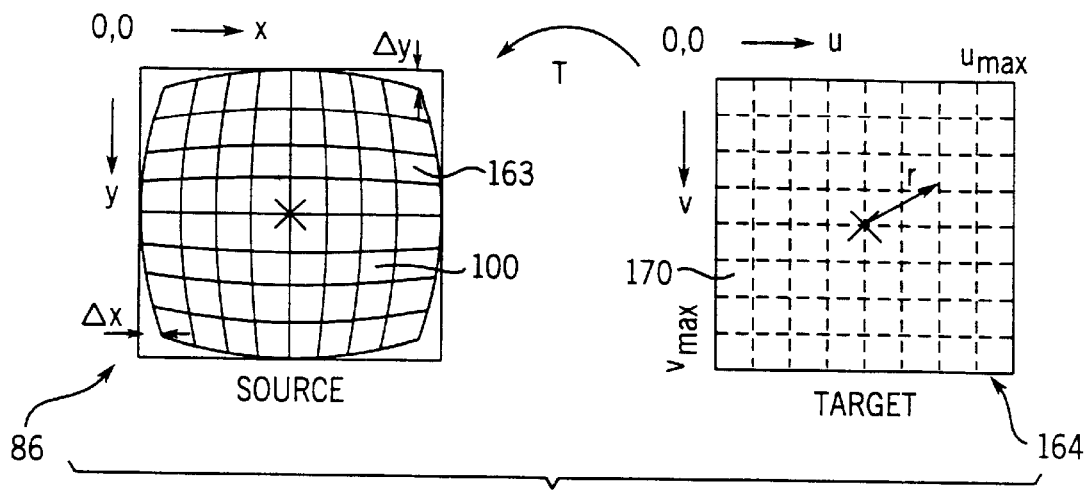
FIG. 19 is a schematic representation of a distorted image of FIG. 11 and a schematic representation of a corresponding undistorted image showing the variables used in the mathematical transformation of the distorted image to correct for rotation and distortion.

Referring to FIG. 19, there are two types of distortion, isotropic and anisotropic. Isotropic distortion is rotationally symmetric (e.g. like barrel and pin cushion distortion). Anisotropic distortion is not rotationally symmetric. Both types of distortion and rotation are so-called third order aberrations which can be written in the form:

$$Dx = r^2(Du - dv) \quad (2)$$

$$Dy = r^2(Dv + du) \quad (3)$$

where Dx and Dy are pixel shifts due to distortion; r is the distance from the correct position to the optical axis and D and d are distortion coefficients which are constant and u and v are correct pixel positions.

Referring also FIG. 2, received image 86 may exhibit pin cushion distortion evident if an image 86 of the rectilinear grid 100 is made. The distortion is caused by the pixel shifts described above.

Equations 1 and 2 may be rewritten as third order two-dimensional polynomials, the case for equation (1) following:

$$x = (a_x + e_x v + i_x v^2 + m_x v^3) + (b_x + f_x v + j_x v^2 + n_x v^3)u + (c_x + g_x v + k_x v^2 + o_x v^3)u_2 + (d_x + h_x v + l_x v^2 + p_x v^3)u^3 \quad (4)$$

In these polynomials, ax and ay govern the x and y translation of the image, ex and by take care of scaling the output image, while ey and bX enable the output image to rotate. The remaining higher order terms generate perspective, sheer and higher order distortion transformations as will be understood to those of ordinary skill in the art. Thirty-two parameters are required for the two, third order polynomials. These parameters may be automatically extracted by imaging the known grid 100 and comparing the distorted image of the grid 100 to the known grid 100 to deduce the degrees of distortion.

Referring now to FIG. 19 in a first step of the correction process, the grid 100 is imaged as indicated by process block 160 to determine the exact type of distortion present and to obtain values for the coefficients a through p of the above referenced polynomial equations.

At process block 166, these parameters may be input to the electronic computer 22 and used at a transformation of received image 86 into image data 164 as indicated by process block 168. For rotation of the image 164, new parameters of the polynomials may be entered by means of hand-held remote control wand 63 shown in FIG. 1.

The transformation process generally requires a determination of the pixel shift for each radiation pixel of the input image 86 which in turn requires an evaluation of the polynomials whose coefficients have been input. A number of techniques are known to evaluate such polynomials including a forward differencing technique or other techniques known in the art. These transformations provide values of u and v for an image pixel 170 corresponding to a particular radiation pixel 163.

After the transformation of process block 168, the u, v locations of the radiation pixels will not necessarily be centered at a pixel location defined by the hardware of the computer monitor 18 which usually spaces pixels 170 at equal distances along a Cartesian axis. Accordingly, the transformed pixels must interpolated to actual pixel locations as indicated by process block 172.

A number of interpolation techniques are well known including bilateral and closest neighbor interpolation, however in the preferred embodiment, a high resolution cubic spline function is used. A given value of an interpolated pixel 170 (Pi,t) is deduced from a 4×4 block of transform pixels (Pi,j) in which it is centered as follows:

$$P_{int} = f(n-2)X_1 + f(n-1)\ x_2 + f(n)X_3 + f(n+1)X_4 \quad (5)$$

where:

$$Xi = f(m-2)P_{i,i} + f(m-1)\ P_{i,2} + f(m)P_{i,2} + f(m+1)P_{i,4} \quad (6)$$

where:

$$f(x) = (a+2)x^3 + -(a+3)\ x^2 + 1 \text{ for } x \in [0,1];$$

$$f(x) = ax^3 + -5\ ax^2 + 8\ ax - 4a \text{ for } x \in [1,2]; \quad (7)$$

f(x) is symmetrical about zero. In the preferred embodiment a=−0.5 and where m and n are fractions indicating the displacement of the neighboring pixels $P_{i,j}$ with respect to $P_{int}$ in the x and y directions, respectively.

At process block 180, the transformed and interpolated image is displayed.

Noise Equalization

Figure 12:
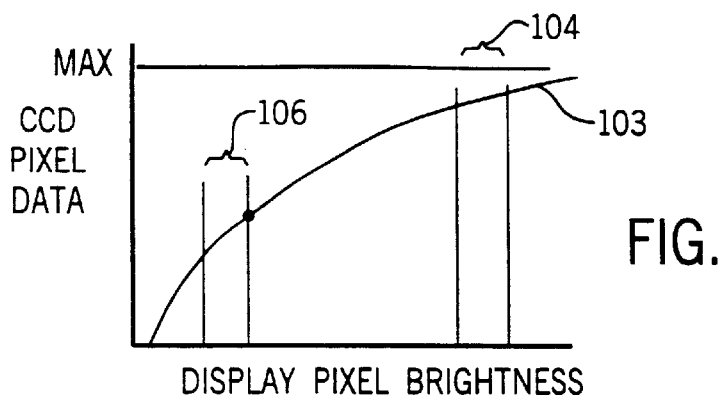
FIG. 12 is a plot of raw image data from the image intensifier/video camera as is translated into pixel brightness in the images of FIGS. 7, 8, 10, and 11 by the microprocessor of FIG. 6 according to a non-linear mapping process such as provides noise equilibrium in the images and maximum dynamic range for clinical data.

Referring now to FIG. 12, the radiation data from the CCD camera 84 are mapped to the brightness of the pixels of the image 86 according to a second transformation. In the preferred embodiment, this mapping between CCD radiation data and image pixel brightness follows a nonlinear white compression curve 103 based on the hyperbolic tangent and being asymptotically increasing to the maximum CCD pixel value. This curve is selected from a number of possibilities so that equally wide bands of image pixel brightness 104 and 106 have equal amounts of image noise. The curve 103 is further positioned to provide the maximum contrast between clinically significant tissues in the image.

Exposure Control

The noise in the image 86 is further reduced by controlling the fluence of the x-ray beam 80 as a function of the density of tissue of the patient within the beam 80. This density is deduced from the image 86 itself produced by the CCD camera 84. In response to the image data, a control signal is sent via the fiber optic strand within the cable 60 to the x-ray tube power supply 74 positioned adjacent to the x-ray tube 68 ((shown in FIG. 5). By positioning the x-ray tube power supply 74 near the x-ray tube 68, extremely rapid changes in the power supplied to the x-ray tube 68 may be obtained. Distributed capacitances along high tension cables connecting the x-ray tube 68 to a stationary x-ray tube power supply are thus avoided in favor of low voltage cable 60, and the shielding and inflexibility problems with such high tension cables are also avoided.

Automatic Technique Control

Figure 13:
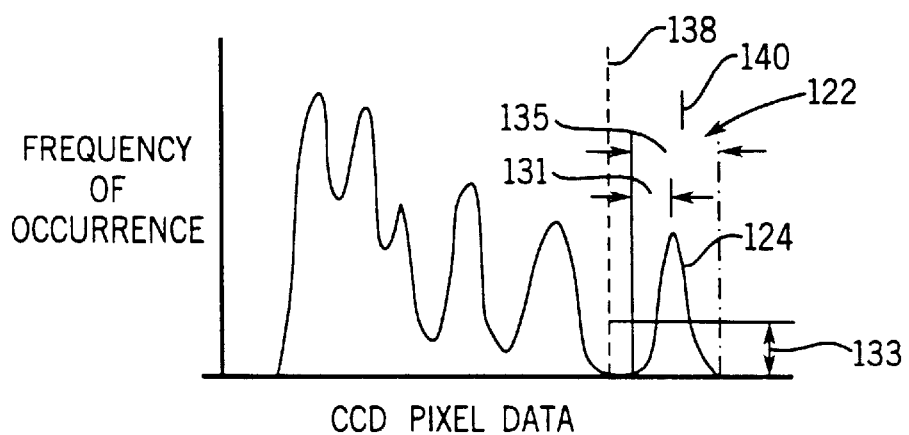
FIG. 13 is a histogram plotting values of data from the image intensifier/video camera versus the frequency of occurrence of data values showing an isolated Gaussian distribution at the right most side representing unattenuated x-ray values.
Figure 14:
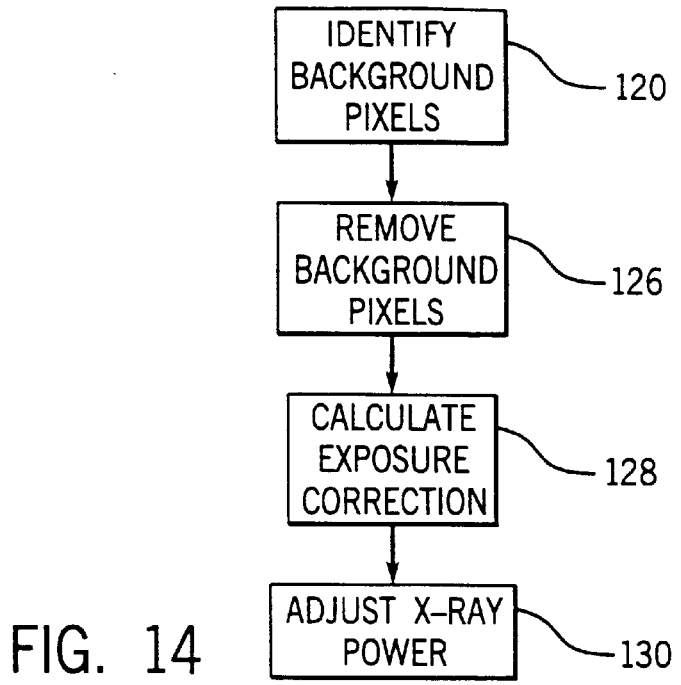
FIG. 14 is a flowchart describing the steps taken by the programmed microprocessor of FIG. 6 to identify background pixels and remove them from a calculation of exposure rate used for controlling the remote x-ray tube power supply of FIG. 6.
Figure 20:
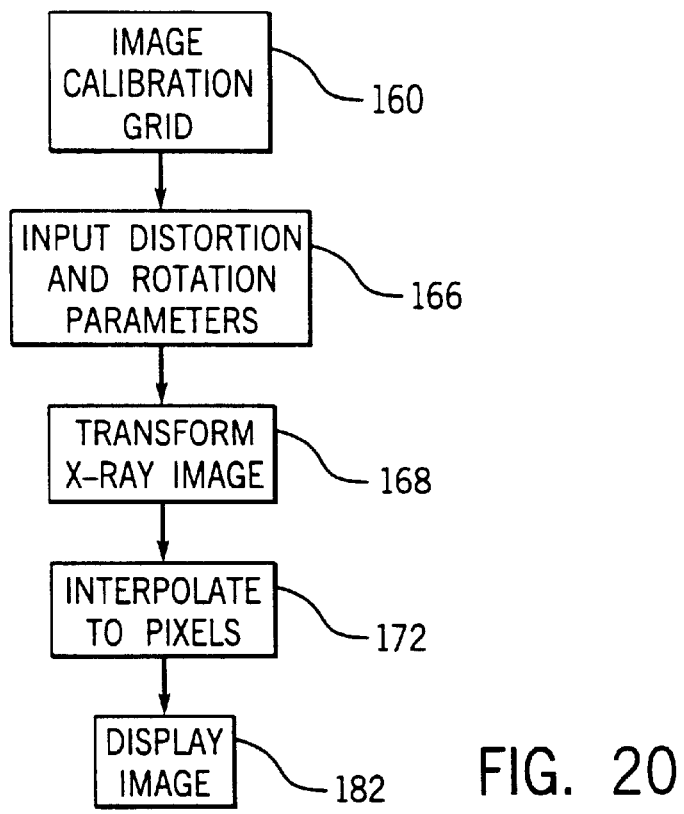
FIG. 20 is a flow chart of the steps performed by the electronic computer in correcting and transforming the image of FIGS. 11 and 19.

Referring now to FIGS. 13 and 14, a determination of the proper control signal to send to the x-ray tube power supply 74 begins by analyzing the image data 86 as shown in process block 120. The goal is to provide for proper exposure of an arbitrary object placed within the x-ray beam 80 even if it does not fill the field of view of the CCD camera 84. For this reason, it is necessary to eliminate consideration of the data from the CCD camera 84 that form pixels in the image corresponding to x-rays that bypass the imaged object and are unattenuated ("background pixels"). These background pixels may be arbitrarily distributed in the image 86 and therefore, this identification process identifies these pixels based on their value. To do this, the computer 22 collects the values of the pixels from the CCD camera 84 in a histogram 122 where the pixels are binned according to their values to create a multiple peaked plot. The horizontal axis of the histogram 122 may for example be from 0 to 255 representing 8 bits of gray scale radiation data and the vertical axis may be a number of pixels having a particular value.

If there is a histogram value at horizontal value 255, and the maximum gray scale exposure recorded, the entire area of the histogram 122 is assumed to represent the imaged object only (no background pixels). Such a situation represents an image of raw radiation only or a high dose image of a thin object with possible clipping. In assuming that the whole histogram 122 may be used to calculate technique without removal of background pixels, a reduced exposure rate will result as will be understood from the following description and the peak classification process, to now be described, is skipped. Otherwise, if there are no pixels with the maximum value of 225, the present invention identifies one peak, 124 in the histogram 122 as background pixels indicated by process block 120 in FIG. 14. In identifying this peak 124, the computer 22 examines the histogram 122 from the brightest pixels (rightmost) to the darkest pixels (leftmost) assuming that the brightest pixels are more likely to be the unattenuated background pixels. The process block 120 uses several predetermined user settings as will be described below to correctly identify the peak 124.

Once the peak 124 has been identified, the pixels associated with that peak are removed per process block 126 by thresholding or subtraction. In the thresholding process, pixels above a threshold value 138 below the peak 124 are considered to be background pixels and are omitted from an exposure rate calculation. In the subtraction method, the peak 124 itself is used as a template to identify pixels which will be removed.

At process block 128, an exposure rate is calculated based on the values of the pixels in the remaining histogram data and at process block 130, an amperage and voltage value are transmitted via the cable 60 to the x-ray tube power supply and used to change the power to the x-ray tube. Generally, if the exposure rate is above a predetermined value, the amperage and voltage are adjusted to cut the x-ray emission from the x-ray tube, whereas if the exposure rate is below the predetermined value, the amperage and voltage are adjusted to boost the exposure rate to the predetermined value.

Figure 15:
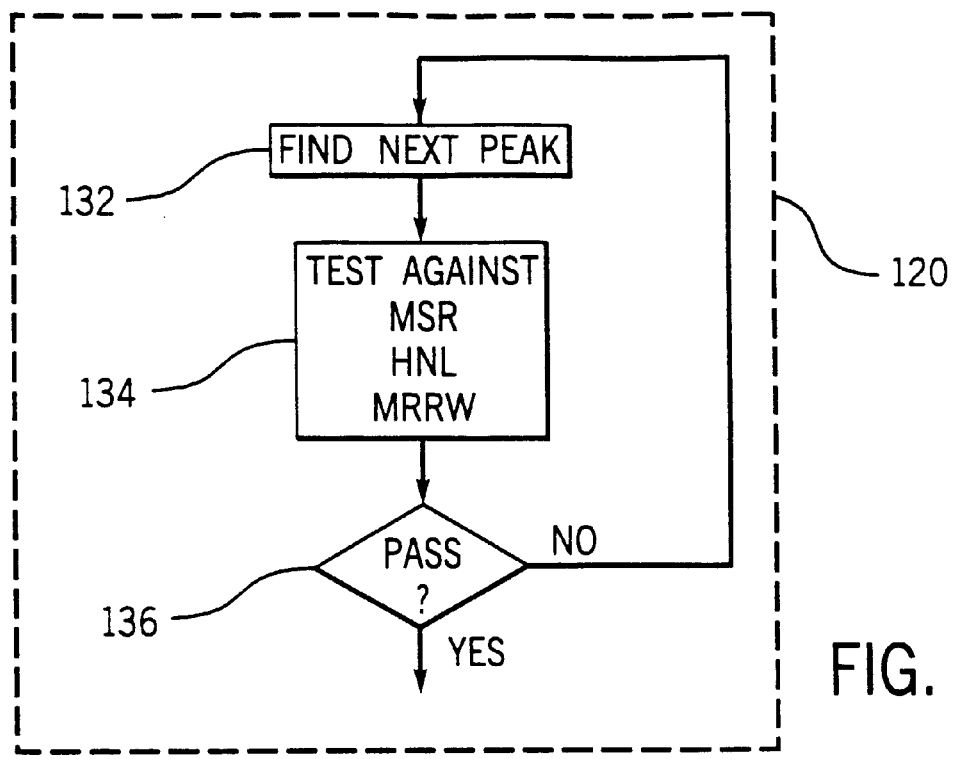
FIG. 15 is a detailed block diagram of the first block of the flow chart of FIG. 14.

Referring now to FIGS. 13, 14 and 15, the process of identifying background pixels will be explained in more detail. Process block 120 includes as a first step, an identification of a right most peak 124 in the histogram 122 (shown in FIG. 13) as indicated by subprocess block 132.

At succeeding subprocess block 134, this right most peak 124 is compared against three empirically derived parameters indicated in the following Table 1:

TABLE 1

| | |
|---|---|
| Minimum Slope Range (MSR) | Minimum necessary pixel range for which the slope of the peak must be monitonically increasing. |
| Histogram Noise Level (HNL) | Minimum height of the maximum value of the peak. |
| Maximum Raw Radiation Width (MRRW) | Maximum width of the detected peak with respect to the width of the entire histogram. |

Specifically at subprocess block 134, each identified peak 124 is tested against the three parameters indicated in Table 1. In the description in Table 1, "width" refers to the horizontal axis of the histogram 122 and hence a range of pixel values, whereas "height" refers to a frequency of occurrence for pixels within that range, i.e., the vertical axis of the histogram 122.

These first two tests, MSR and HNL, are intended to prevent noise peaks and peaks caused by bad imaging elements in the CCD camera 84 or quantization of the video signal in the A to D conversion from being interpreted as background pixels.

Peaks 124 with a suitable stretch of monotonically increasing slope 131 (shown in FIG. 13) according to the MSR value and that surpass the histogram noise level HNL 133 are evaluated against the MRRW parameter. This third evaluation compares the width 135 of the histogram 122 against the width of the entire histogram 122. The MRRW 20 value is intended to detect situations where the imaged object completely fills the imaging field and hence there are no unattenuated x-ray beams or background pixels being detected. A valid peak 124 will normally have a width 135 more than 33% of the total width of the histogram 122.

At decision block 136 if the peak 124 passes the above tests, the program proceeds to process block 126 as indicated in FIG. 14. Otherwise, the program branches back to process block 132 and the next peak to the left is examined against the tests of process block 134 until a passing peak is found or no peak is found. If no peak is found, it is assumed that there are no background pixels and a raw exposure value is calculated from all pixels as described above.

Figure 16:
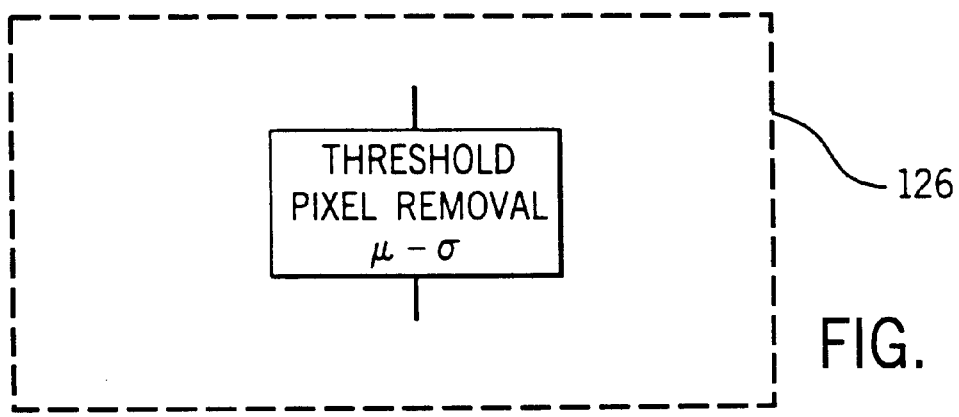
FIG. 16 is a first embodiment of the second block of the flow chart of FIG. 14.
Figure 17:
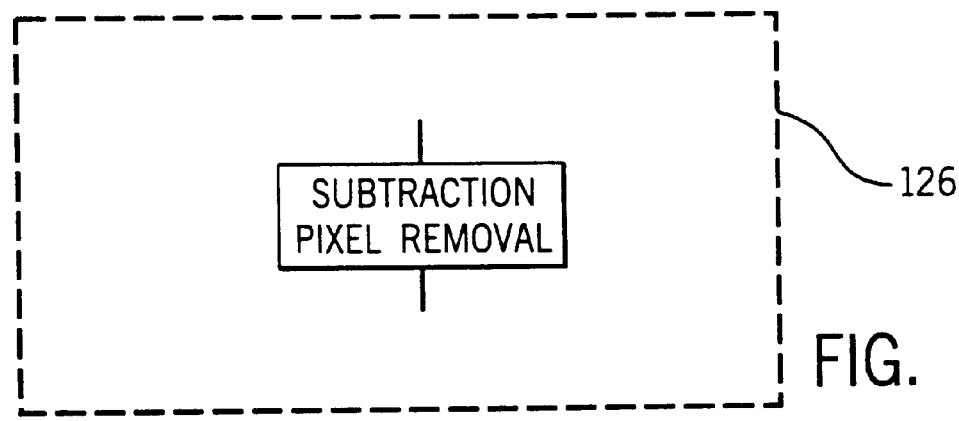
FIG. 17 is a second embodiment of the second block of the flow chart of FIG. 14.

Assuming that a peak 124 passes the tests of Table 1, then at process block 126 background pixels identified by the peak 124 selected at process block 120 are eliminated. In a first method of eliminating background pixels indicated at FIG. 16, a magnitude threshold 138 within the histogram 122 is identified. Pixels having values above this threshold will be ignored for the purpose of selecting an exposure technique. The threshold 138 is established by identifying the center 140 of the peak 124 (its maximum value) and subtracting from the value of the center a value s being the distance between the start of the peak 124 as one moves leftward and the maximum 140.

The area under the histogram 122 for values lower than the threshold 136 is computed to deduce a raw exposure value which will be used as described below. In a second embodiment, the shape of the histogram peak 124 from the start of the peak as one moves leftward to its maximum 140 is reflected about a vertical line passing through the maximum 140 and subtracted from the histogram peak 124 to the left of the vertical line. This approach assumes that the peak 124 of the background pixels is symmetrical and thus this method better accommodates some overlap between the object pixels and the background pixels in the histogram 122. Again, the remaining pixels of the histogram 122 are summed (by integration of the area under the histogram 122 minus the area of the peak 124 as generated by the reflection) to provide a raw exposure value.

Figure 18:
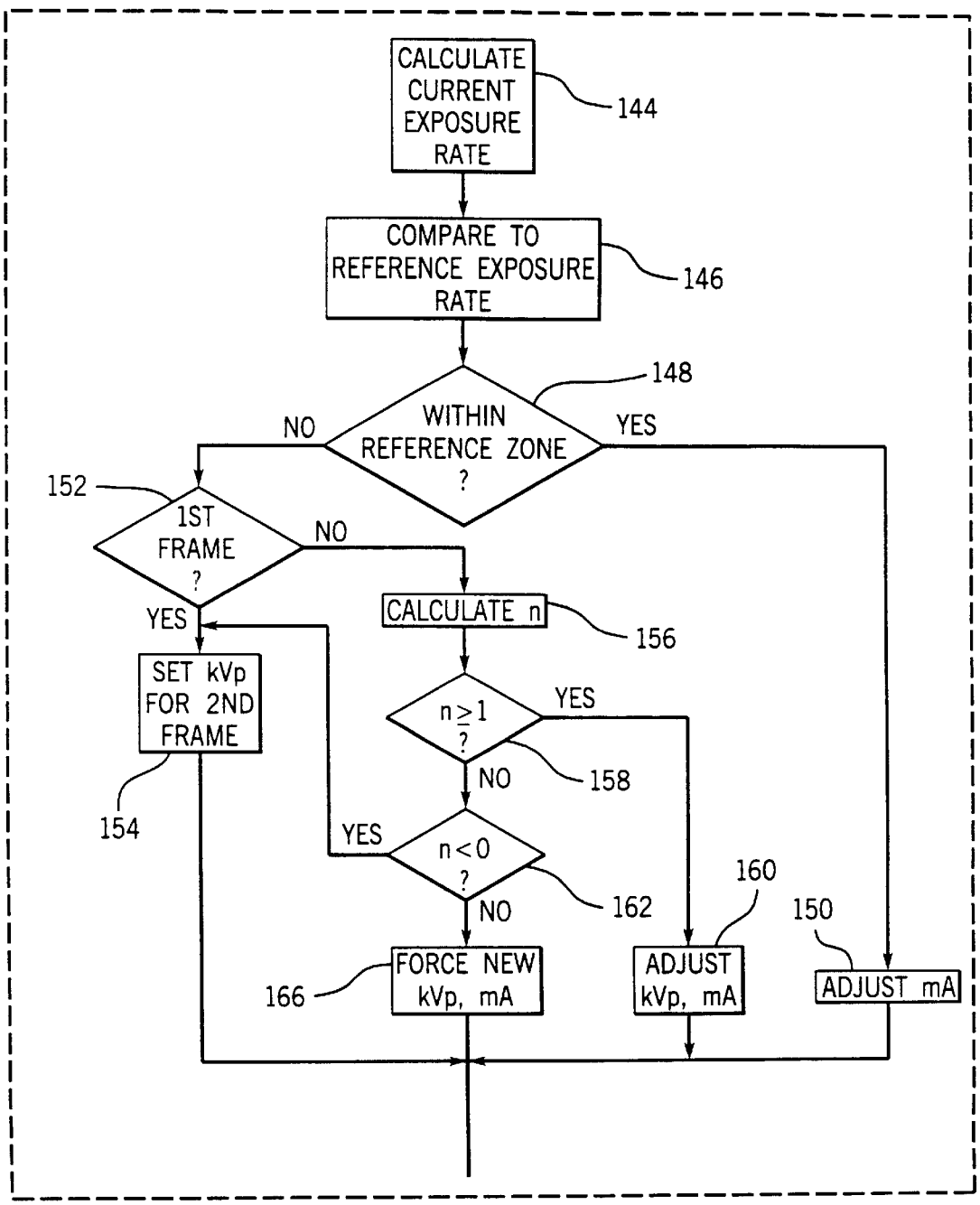
FIG. 18 is a detailed flow chart of the third block of the flow chart of FIG. 14.

Referring now to FIG. 18, the raw exposure value is transformed by the known transfer characteristics of the CCD camera (relating actual x-ray dose to pixel value) to produce a calculated current exposure rate as indicated at process block 144.

Referring to process block 146, the current exposure rate is next compared to a reference exposure rate, in the preferred embodiment being 1.0 mR per frame. If at process block 148 the current exposure rate is within a "half fine-tune range" of the reference exposure rate, then the program proceeds to process block 150, a fine tuning process block, and the amperage provided to the x-ray tube are adjusted in accordance to the disparity between the amperage and reference exposure rate. That is, if the current exposure is greater than the reference exposure rate, the amperage to the x-ray tube is reduced.

The new value of amperage is compared against a predetermined range of amperage values (maximum beam current and minimum beam current values) so that the amperage value may never vary outside of this range.

If at decision block 148 the current exposure rate is outside of the half fine tune range established at decision block 148, a more substantial adjustment process is undertaken. Generally, the exposure provided by an x-ray system will follow the following equation:

$$X \approx mA \, kVp^n. \tag{8}$$

where:

mA is the amperage provided to the x-ray tube, kVp is the voltage provided to the x-ray tube, and n is a power factor dependent on the geometry of the machine and the particular kind of object being imaged.

Generally, the value of n will not be known in advance. Accordingly in the more substantial correction process, n is deduced by obtaining two different exposures with different kVp values so that the value of n may be deduced.

At decision block 152 it is determined whether a first or second reference exposure is to be obtained. If the first reference exposure was just obtained, the program proceeds to process block 154 and a new value of kVp is determined for a second exposure. In this case, the first exposure used will be that which was employed to produce the histogram 122 as previously described.

If the comparison of process block 148 indicated that the exposure rate was too high, a lower kVp value is selected; and conversely, if the exposure at process block 148 indicated the exposure was too low, an increased value of kVp is provided. The new kVp value for the second exposure must be within a predetermined range of kVp values established by the user. Mathematically, the kVp value selected may be described as:

$$kVp_2 = kVp_1 + a(dkVp) \tag{9}$$

where a is a step factor and dkVp is a minimum practical change in tube voltage.

Two preferred means of selecting may be used: one providing linear and one providing logarithmic scaling. Such scaling techniques are well understood to those of ordinary skill in the art.

If at decision block 152, a second frame-has already been taken with the new voltage value, then the program proceeds to process block 156 and the value of n in equation (9) is calculated. If the value of amperage is held constant between the first and second frame, the value of n may be determined according to the following equation:

$$n = \log \frac{X_2}{X_1} \bigg/ \log \frac{kVp_2}{kVp_1} \tag{10}$$

where $X_1$ and $X_2$ are the measured exposure rates at the first and second frames, respectively and $kVp_1$ and $kVp_2$ are the two x-ray tube voltages during the first and second frames.

At process block 158, this value of In, is checked against threshold values intended to detect whether an erroneous value of n has been produced as a result of clipping, in the radiation data used to calculate exposure. As is understood in the art, clipping occurs when an increased dose of an element of the CCD camera produces no increase in the camera's output.

At decision block 158, if the value of n calculated at process block 156 is greater than or equal to one, it is assumed to be valid and the program proceeds to process block 160 where kVp and mA are adjusted by setting mA equal to a maximum reference value and calculating kVp according to the following equation:

$$kVp_{new} = kVp_2 \left( \frac{X_{ref} mA_2}{X_2 mA_{ref}} \right) 1/n$$

where $kVp_{new}$ and $mA_{new}$ are the settings for the next frame to be shot. If the resulting kVp value conflicts with the minimum system, kVp, kVp is set to the minimum system value and mA is calculated according to the following equation using the mA and kVp value of the second frame.

$$mA_{new} = mA_2 \frac{X_{ref}}{X_2} \left( \frac{kVp_2}{kVp_{min}} \right)^n \tag{12}$$

If the value of n in decision block 158 is less than 10 one then at process block 162 n is tested to see if it is less than zero. This value of n is realized when the exposure rate of the second frame changes in the opposite direction of the tube voltage. This suggests a clipped histogram and therefore the program branches back to process block 154 to obtain a new second frame. This condition may also arrive from object motion between the first and second frame.

On the other hand, if at decision block 162 n is not less than zero (e.g. n is between zero and 1)., the program proceeds to process block 166. Here it is assumed that because the sensitivity of the exposure rate on change in kVp is low, there may be some partial clipping. New values of kVp and mA are then computed and used with the previous second frame values to calculate a new n as 25 follows. Generally, if kVp and mA are high, they are both lowered and if kVp and mA are low they are both raised.

This automatic control of the x-ray technique, based on a portion of the field of view of the x-ray machine (e.g., based on a type of material) may be extended to optimize exposure for a particular structure within the [Hrt]32 field of view, for example, for bone over soft tissue. In this case, the analysis of the histogram described is adjusted to identify bone pixels and those are used for the technique control. As another example, the method may be used to provide optimal exposure of a contrast agent in blood vessels. This process may also be refined through the use of a dual energy x-ray beam and prior art dual energy analysis which allow different basis materials within an imaged object to be identified according to their attenuation characteristics at the two energy levels. Using dual energy x-rays, permits bone pixels to be extracted from the image (regardless of absolute attenuation) and used for the exposure control as described above.

If Similarly, the technique is not limited to medical imaging but may be used in other areas such as in baggage scanning where it is desired to optimize the image based not on the entire field of view (luggage and air) or a predefined portion of the field of view but based on arbitrary regions defined by the structures actually imaged (e.g., explosives or metallic structures).

Scatter Reduction

Referring now to FIG. 1, the image produced by the present invention may be used for quantitative analysis including, for example, that of making the bone density measurement. It is known to make bone density analysis from x-ray images through the use of dual energy techniques in which the voltage across the x-ray tube is changed or a filter is periodically placed within the x-ray beam to change the spectrum of the x-ray energy between two images. The two images may be mathematically processed to yield information about different basis materials within the image object (e.g. bone and soft tissue). For these quantitative measurements, it is desirable to eliminate the effect of scatter.

Figure 23:
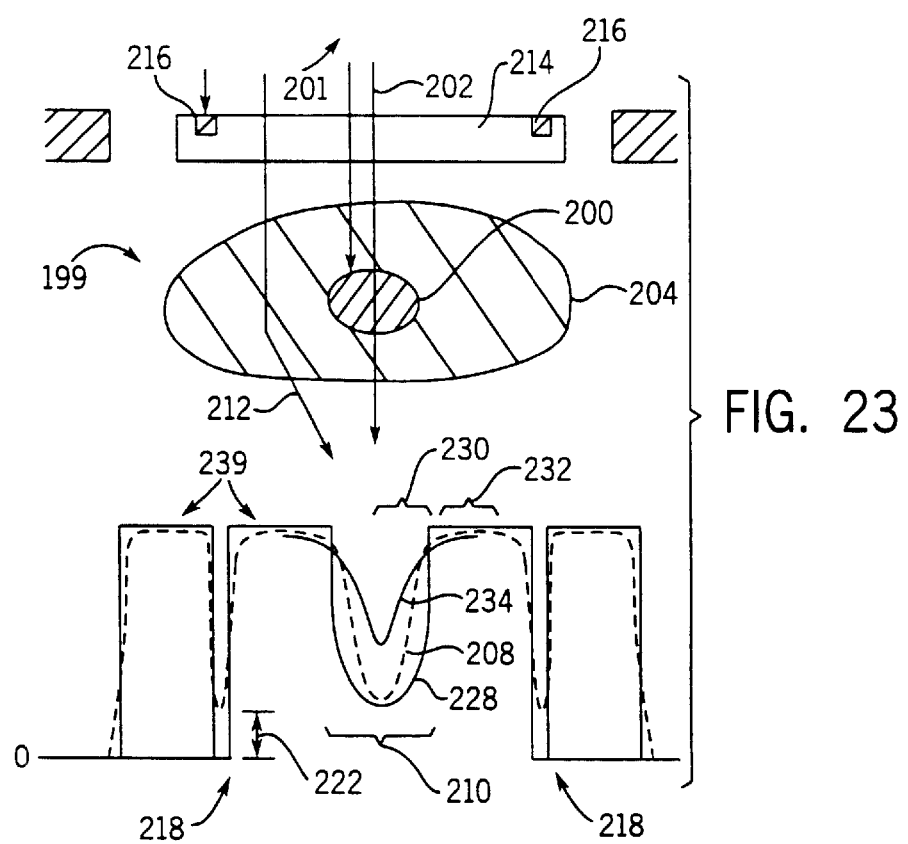
FIG. 23 is a cross-sectional view through the occluder of an imaged object of FIG. 21 along line 23—23, aligned with a graph depicting attenuation of x-rays as a function distance along the line of cross-section as well as theoretical attenuation without scatter and scatter components.

Referring now to FIG. 23 in imaging a patient's spine 200, for example, x-rays 202 are directed from an x-ray source 201 through the patient 199 to pass through soft tissue 204 surrounding a spine 200 and the spine 200. Certain of the x-rays 202 are blocked by the spine 200 and others pass through the spine 200 to be recorded at the image intensifier 206. An attenuation image 208 measured by an image intensifier measures those x-rays passing through the patient 109.

A portion 210 of the attenuation image directly beneath the spine 200 records not only those x-rays 202 passing through the spine 200 and the soft tissue 204 above and below it, but also scattered x-rays 212 directed, for example, through soft tissue 204 to the side of the spine 200 but then scattered by the soft tissue to proceed at an angle to the portion 210 of the attenuation image 208 beneath the spine 200. Because the scattered x-rays 212 do not carry information about the attenuation of the spine 200, they are desirably removed from the image 208 prior to its use in quantitative measurement.

For this purpose, the present invention uses an occluder 214 being an x-ray transparent plate such as may be constructed of PLEXIGLAS and incorporating into its body, a plurality of x-ray blocking lead pins 216. Preferably these pins are placed so as to project images 218 onto the image 208 received by the image intensifier 206 in positions outside an image 220 of the spine 200. Generally therefore, the pins 216 are placed at the periphery of the occluder 214. The pins 216 are sized so as to substantially block all direct x-rays from passing through them but so that their images 218 include a significant portion of scattered x-rays 212.

Figure 22:
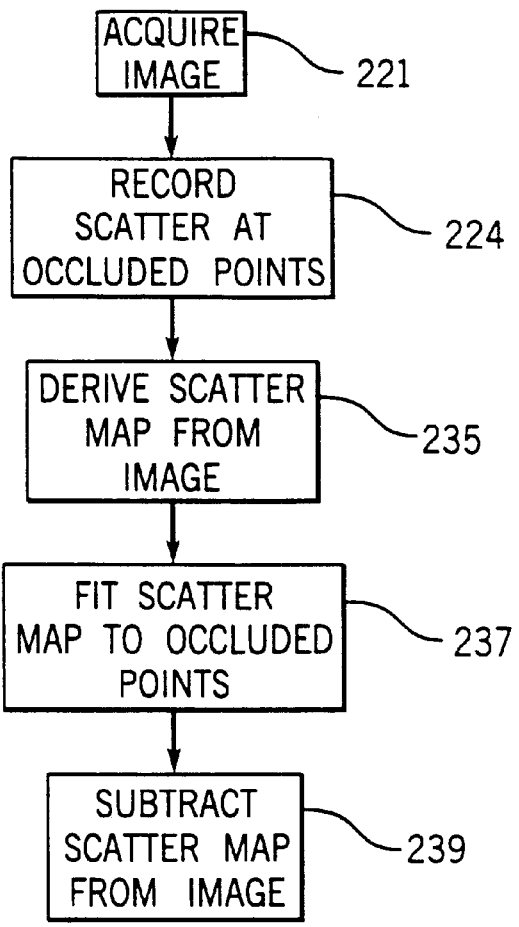
FIG. 22 is a flow chart of the steps of calculating and removing scatter using the occluder of FIG. 21.
Figure 21:
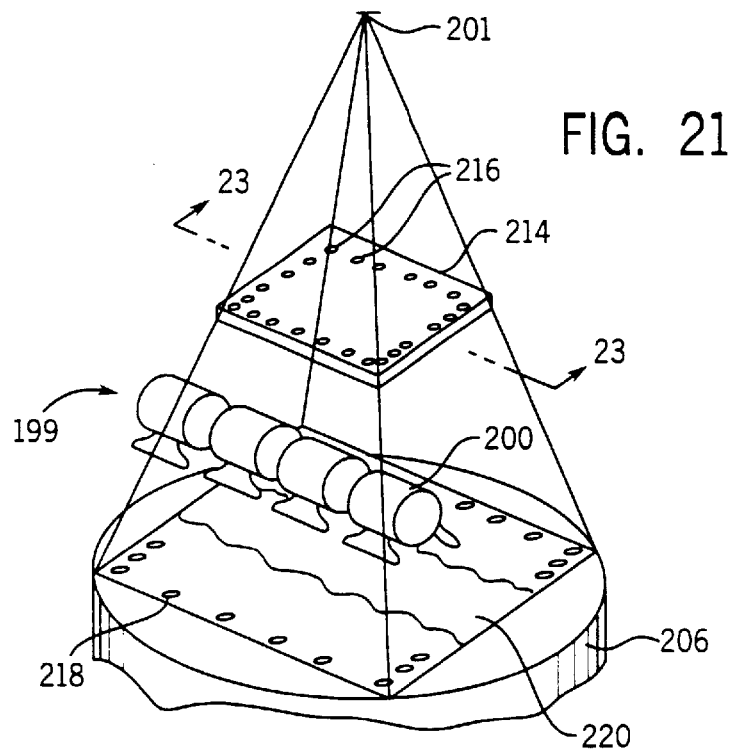
FIG. 21 is a perspective view of an occluder placed in an x-ray beam prior to an imaged object and used for calculating scatter.

Referring now to FIG. 22 at a first step of a scatter reduction operation with the occluder 214 of FIG. 21, an image is acquired of the imaged object, for example, the spine 200 and its surrounding soft tissue 204 (not shown in FIG. 21) including the images 218 of the pins 216. This acquisition is indicated by process block 221 of FIG. 22. The pins 216 are held in predetermined locations with respect to the image 208 so that their images 218 may be readily and automatically identified.

At each pin image 218, a value 222 indicating the magnitude of the received x-rays, shown in FIG. 23, may be ascertained. This value 222 measures the scatter received in the vicinity of image 218 caused generally by the effect of the soft tissue 204 and possible secondary scatter effects in the image intensifier 206. Values 222 are recorded, as indicated by process block 224, for each pin image 218. From these values, a set of normalizing points are established.

The image 208 is then used to derive a scatter map. Referring to FIG. 23, generally the amount of scatter at a given point will be a function of how many x-ray photons are received at points adjacent to the given point. For example, comparing the image 208 to a theoretical scatter-less image 228 generally in an attenuated region 230 of the image 208 (e.g., under the spine 200 ), scatter will increase the apparent value in the image 208 as a result of radiation from nearby low attenuation regions scattering into the high attenuation region 230. Conversely the apparent value at a low attenuation region 232 will be decreased because of the scatter into the high 5 attenuation region.

A map of the scattered radiation may thus be modeled by "blurring" the image 208. This blurring can be accomplished by a low pass filtering of the image 208, i.e., convolving the image 208 with a convolution kernel rectangular dimensions having corresponding to the desired low pass frequency cut off. The effect is an averaging of the image 208 producing scatter map 234.

The image used to produce the scatter map 234 is an attenuation image 208 obtained from the patient 199 without the occluder 214 in place, or may be an image 208 including the images 218 of the pins 216 but with the latter images 218 removed based on knowledge of their location. This removal of images 218 may substitute values of the image 208 at points 239 on either side of the images 218. The process of driving the scatter map from the image is indicated by process block 235 of FIG. 24.

Next as indicated by process block 237, the scatter map 234 is fit to the normalizing points 222 previously determined at process block 224.

Figure 24:
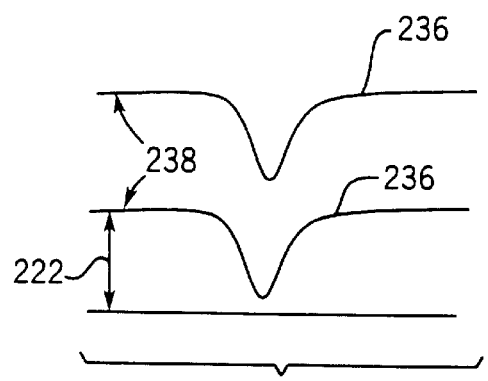
FIG. 24 is a graphical representation of an adjustment of calculated scatter from the image of FIG. 23 based on normalizing points established by the occluder of FIG. 21.

Referring to FIG. 24, the scatter map 234 is thus normalized so that the portions 238 of the scatter map 236 located near the places where the images 218 would fall are given values 222 as determined at process block 224. This involves a simple shifting up or down of the scatter map 236 and may employ a "least square" fit to shift the scatter map 236 to multiple values 222 obtained from each pin 216. As adjusted, the scatter map 236 is then subtracted from the image 208 to eliminate or reduce the scatter in that image as indicated by process block 239.

The effect of subtracting a low pass filtered or blurred image properly normalized to actual scatter is to sharpen up the image 208 but also to preserve its quantitative accuracy. Thus the present invention differs from prior art scatter reduction techniques in that it both addresses the variation in scatter across the image caused by attenuation of x-rays by the imaged object but also incorporates accurate measurements of scatter in certain portions of the image.

It is thus envisioned that the present invention is subject to many modifications which will become apparent to those of ordinary skill in the art. Accordingly, it is intended that the present invention not be limited to the particular embodiment illustrated herein, but embraces all such modified forms thereof as come within the scope of the following claims.

We claim:

1. An x-ray imaging system comprising:
   an x-ray tube positioned on one side of an object;
   an imaging x-ray detection chain positioned on an opposite side of the object from the x-ray tube producing distorted x-ray detection signals each related to x-rays received at an imaging surface at different spatial locations;
   an electronic display displaying pixels at image locations;
   an electronic computer receiving the distorted x-ray detection signals and operating according to a stored program to illuminate a pixel at a particular image location based on the value of a signal received at a particular spatial location as related to the particular image location by a mathematical transformation.

2. The x-ray imaging system of claim 1 wherein the x-ray detection chain includes a scintillator, an image intensifier and a camera.

3. The x-ray imaging system of claim 1 wherein the value of a signal received at a particular spatial location is stored in an electronic memory associated with the electronic computer and wherein the illumination of the pixel uses the value of the signal received at the particular spatial location as stored in memory.

4. The x-ray imaging system of claim 1 wherein the electronic computer operating according to the stored program corrects for at least one of the group consisting of: rotation, isotropic distortion and anisotropic distortion.

5. The x-ray imaging system of claim 1 wherein the mathematical transformation solves a third order two-dimensional polynomial equation relating spatial locations to image locations.

6. The x-ray imaging system of claim 1 wherein the electronic computer operating according to the stored program further interpolates the signal received at the particular spatial location to the image location of the pixel.

7. The x-ray imaging system of claim 6 wherein the interpolation employs a cubic spline function.

* * * * *